US011884901B2

(12) United States Patent
Kotsakis et al.

(10) Patent No.: US 11,884,901 B2
(45) Date of Patent: Jan. 30, 2024

(54) MOUSSE COMPOSITION

(71) Applicant: Conopco, Inc., Englewood Cliffs, NJ (US)

(72) Inventors: Panagiotis Kotsakis, Athens (GR); Neil James Parry, Tarporley (GB); Keith Leslie Rutherford, Heswall (GB); Simon John Moore, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 529 days.

(21) Appl. No.: 17/272,382

(22) PCT Filed: Sep. 6, 2019

(86) PCT No.: PCT/EP2019/073906
§ 371 (c)(1),
(2) Date: Mar. 1, 2021

(87) PCT Pub. No.: WO2020/053108
PCT Pub. Date: Mar. 19, 2020

(65) Prior Publication Data
US 2021/0332310 A1 Oct. 28, 2021

(30) Foreign Application Priority Data
Sep. 14, 2018 (EP) ..................... 18194562

(51) Int. Cl.
| | | |
|---|---|---|
| C11D 1/00 | (2006.01) |
| C11D 3/18 | (2006.01) |
| C11D 3/32 | (2006.01) |
| C11D 7/24 | (2006.01) |
| A61K 8/31 | (2006.01) |
| A61K 8/34 | (2006.01) |
| A61K 8/42 | (2006.01) |
| C11D 11/00 | (2006.01) |
| C11D 3/00 | (2006.01) |
| C11D 3/20 | (2006.01) |
| C11D 7/32 | (2006.01) |
| C11D 17/00 | (2006.01) |

(52) U.S. Cl.
CPC ........ *C11D 11/0058* (2013.01); *C11D 3/0094* (2013.01); *C11D 3/201* (2013.01); *C11D 3/2068* (2013.01); *C11D 7/3281* (2013.01); *C11D 17/0043* (2013.01)

(58) Field of Classification Search
CPC .......... C11D 1/00; C11D 3/18; C11D 3/2006; C11D 3/2068; C11D 3/32; C11D 7/24; C11D 7/261; C11D 7/263; C11D 7/3281; C11D 17/0043; A61K 8/31; A61K 8/34; A61K 8/42; A61K 8/4906
See application file for complete search history.

(56) References Cited

U.S. PATENT DOCUMENTS

| | | | |
|---|---|---|---|
| 6,413,529 B1 | 7/2002 | Beerse et al. |
| 6,432,423 B1 | 8/2002 | Maignan et al. |
| 9,586,901 B2 | 3/2017 | Kumar et al. |
| 2002/0031478 A1 | 3/2002 | Keller et al. |
| 2011/0045037 A1 | 2/2011 | Tamarkin et al. |
| 2014/0323386 A1 | 10/2014 | Matsuzawa et al. |
| 2015/0351393 A1* | 12/2015 | Parry ................ A61Q 5/02 |
| | | | 514/424 |
| 2015/0373970 A1 | 12/2015 | Truong et al. |
| 2017/0096391 A1 | 4/2017 | Kumar et al. |
| 2017/0157175 A1 | 6/2017 | Tamarkin et al. |
| 2018/0084777 A1 | 3/2018 | Jiang |
| 2018/0153804 A1 | 6/2018 | Tamarkin et al. |
| 2018/0228153 A1 | 8/2018 | Price |
| 2018/0244616 A1 | 8/2018 | O'Keeffe et al. |

FOREIGN PATENT DOCUMENTS

| | | |
|---|---|---|
| CN | 1229335 A | 9/1999 |
| CN | 1346263 A | 4/2002 |
| CN | 1346264 A | 4/2002 |
| CN | 101410372 A | 4/2009 |
| CN | 103842491 A | 6/2014 |
| CN | 104981157 A | 10/2015 |
| CN | 105050393 A | 11/2015 |
| CN | 108024939 A | 5/2018 |
| EP | 2778217 A1 | 9/2014 |
| GB | 823062 | 11/1959 |
| WO | 9802044 A1 | 1/1998 |
| WO | 0061107 A1 | 10/2000 |
| WO | WO0240628 | 5/2002 |

(Continued)

OTHER PUBLICATIONS

Search Report and Written Opinion in EP18194524; dated Mar. 28, 2019.
Search report and Written Opinion in EP18194562; dated Feb. 27, 2019.
Search Report and Written Opinion in 18194538; dated Feb. 28, 2019.
Search Report and Written Opinion in PCTEP2019073906: dated Oct. 16, 2019.

(Continued)

*Primary Examiner* — Brian P Mruk

(74) *Attorney, Agent, or Firm* — Carter, DeLuca & Farrell LLP; George Likourezos; Bret P. Shapiro

(57) ABSTRACT

The invention relates to a mousse composition comprising: a) a base composition comprising: (i) from 0.0001 to 5 wt. % of a lactam; (ii) from 0.1 to 10 wt. % of an alcohol; and, b) a propellant; and to the use of a combination of a lactam with an alcohol, in a mousse composition to collapse the resulting mousse foam quicker; and to the use of a combination of a lactam with an alcohol, in a mousse composition to make the resulting mousse foam easier to rinse.

17 Claims, No Drawings

(56) References Cited

FOREIGN PATENT DOCUMENTS

| | | |
|---|---|---|
| WO | WO02092902 | 11/2002 |
| WO | WO2007085042 | 8/2007 |
| WO | WO2009103735 | 8/2009 |
| WO | WO2010125470 | 11/2010 |
| WO | WO2014118240 | 8/2014 |
| WO | WO2017029070 | 2/2017 |
| WO | WO2017108565 | 6/2017 |
| WO | WO2018091222 | 5/2018 |

OTHER PUBLICATIONS

Search Report and Written Opinion in PCTEP2019073895; dated Nov. 15, 2019.
Search Report and Written Opinion in PCTEP201907390; dated Dec. 5, 2019.
Co-pending application, U.S. Appl. No. 17/272,376, filed Mar. 1, 2021.
Co-pending application, U.S. Appl. No. 17/272,378, filed Mar. 1, 2021.

\* cited by examiner

MOUSSE COMPOSITION

FIELD OF INVENTION

The invention relates to a mousse composition.

BACKGROUND OF THE INVENTION

Consumers enjoy using products in the form of a mousse. They are considered luxurious premium products by the consumer, and can be used for many applications by the consumer.

One such application of mousses are in the area of surface care, for example in the treatment of kitchen and bathroom areas by the consumer.

There is therefore a need for a mousse composition that has a foam that collapses quicker, making an easier to rinse product.

SUMMARY OF THE INVENTION

We have found that by incorporation of a lactam with an alcohol in a mousse, the resulting mousse foam collapses quicker, making an easier to rinse product.

This easier to rinse mousse product with quicker collapsing foam has the surprising attribute that the anti-microbrial effect of the lactam is improved in a mousse composition where the foam collapses quicker in comparison to the lactam in a mousse where the foam does not collapse.

The invention relates in a first aspect to a mousse composition comprising:
a) a base composition comprising:
i. from 0.0001 to 5 wt. % of a lactam;
ii. from 0.1 to 5 wt. % of an alcohol; and,
b) a propellant,
wherein the lactam is of formula (I) or (II):

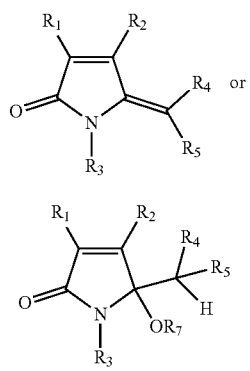

wherein:

$R_1$ and $R_2$ are each independently selected from hydrogen, halogen, alkyl, cycloalkyl, alkoxy, oxoalkyl, alkenyl, heterocyclyl, heteroaryl, aryl and aralalkyl; and $R_3$ is selected from hydrogen, hydroxyl, alkyl, cycloalkyl, alkoxy, oxoalkyl, alkenyl, heterocyclyl, heteroaryl, cycloalkyl, aryl, aralalkyl, —C(O)CR$_6$=CH$_2$, and (CH$_2$)$_n$N$^+$(R$^a$)$_3$, where n is an integer from 1 to 16, preferably 2 to 8, and where each R$^a$ is independently H or C$_{1-4}$ alkyl;

$R_4$ and $R_5$ are independently selected from hydrogen, aryl, heterocyclyl, heteroaryl, and arylalkyl; and $R_6$ is selected from hydrogen and methyl; and
$R_7$ is selected from hydrogen and —C(O)CR$_6$=CH$_2$; and preferably, at least one of $R_4$ and $R_5$ is hydrogen.

The amounts refer to the amount of the specified ingredient present in the base composition.

Preferably the lactam is present at a level of from 0.0001 to 2.5 wt. %, preferably from 0.0001 to 1 wt. %, more preferably from 0.001 to 1 wt. %.

Preferably the alcohol is selected from the group consisting of: phenoxyethanol and ethanol, inclusive of mixtures thereof.

Preferably the lactam of formula (I) or (II), $R_1$, $R_4$ and $R_5$ are H; $R_3$ is H, or (CH$_2$)$_n$N$^+$(CH$_3$)$_3$, where n is an integer from 1 to 16, preferably 2 to 8; and $R_2$ is a phenyl group, or a mono-substituted phenyl group; preferably $R_2$ is selected from phenyl, 4-fluorophenyl, 2-fluorophenyl, 4-chlorophenyl, 3-chlorophenyl, 4-bromophenyl and 4-methylphenyl.

Preferably the lactam is a lactam selected from:

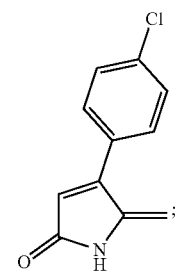

4-(4-chlorophenyl)-5-methylene-pyrrol-2-one; and

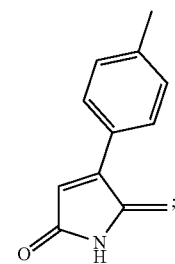

5-methylene-4-(p-tolyl)pyrrol-2-one;

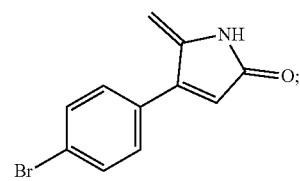

4-(4-bromophenyl)-5-methylene-pyrrol-2-one;

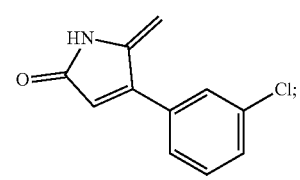

4-(3-chlorophenyl)-5-methylene-pyrrol-2-one;

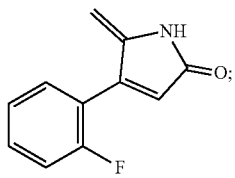

4-(2-fluorophenyl)-5-methylene-pyrrol-2-one; and

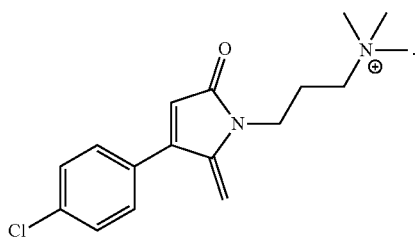 [SMILES: C=C1C(c2ccc(Cl)cc2)=CC(=O)N1CCC[N+](C)(C)C]

Preferably the lactam is in encapsulated form.

Preferably the base composition is present at a level of from 80 to 96 wt. %; and the propellant is present at a level of from 4 to 20 wt. %, more preferably the base composition is present at a level of from 85 to 95 wt. %; and the propellant is present at a level of from 5 to 15 wt. %.

Preferably the propellant is selected from: one or more $C_3$-$C_5$ saturated alkanes or mixtures thereof and dimethyl ether.

Preferably: the base composition comprises one or more of the following ingredients: surfactants, solvents, perfumes, preservatives, thickeners, chelating agents, emulsifiers, pH modifiers, soil removal aids and, hydrotrope.

In a second aspect, the invention relates to the use of a combination of a lactam with an ingredient selected from the group consisting of: phenoxyethanol, ethanol and benzoate (or salt thereof), inclusive of mixtures thereof in a mousse composition to collapse the resulting mousse foam quicker, wherein the lactam is of formula (I) or (II):

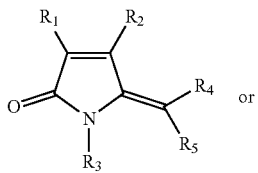

(I)

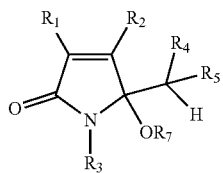

(II)

wherein:

$R_1$ and $R_2$ are each independently selected from hydrogen, halogen, alkyl, cycloalkyl, alkoxy, oxoalkyl, alkenyl, heterocyclyl, heteroaryl, aryl and aralalkyl; and $R_3$ is selected from hydrogen, hydroxyl, alkyl, cycloalkyl, alkoxy, oxoalkyl, alkenyl, heterocyclyl, heteroaryl, cycloalkyl, aryl, aralalkyl, —C(O)CR$_6$=CH$_2$, and (CH$_2$)$_n$N$^+$(R$^a$)$_3$, where n is an integer from 1 to 16, preferably 2 to 8, and where each R$^a$ is independently H or $C_{1-4}$ alkyl;

$R_4$ and $R_5$ are independently selected from hydrogen, aryl, heterocyclyl, heteroaryl, and arylalkyl; and $R_6$ is selected from hydrogen and methyl; and $R_7$ is selected from hydrogen and —C(O)CR$_6$=CH$_2$; and preferably, at least one of $R_4$ and $R_5$ is hydrogen.

The term quicker refers to the speed at which the mousse foam collapses. The mousse foam takes less time (is quicker) to collapse in a mousse comprising the lactam and ingredient selected from phenoxyethanol, ethanol and benzoate than in the same mouse mousse without the lactam and ingredient selected from phenoxyethanol, ethanol and benzoate.

In a third aspect, the invention relates to the use of a combination of a lactam with an ingredient selected from the group consisting of: phenoxyethanol, ethanol and benzoate (or salt thereof), inclusive of mixtures thereof in a mousse composition to make the resulting mousse foam easier to rinse, wherein the lactam is of formula (I) or (II):

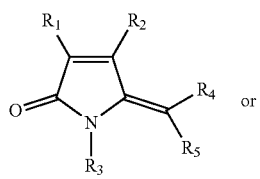

(I)

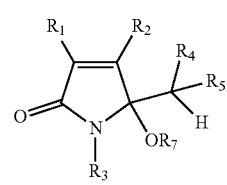

(II)

wherein:

$R_1$ and $R_2$ are each independently selected from hydrogen, halogen, alkyl, cycloalkyl, alkoxy, oxoalkyl, alkenyl, heterocyclyl, heteroaryl, aryl and aralalkyl; and $R_3$ is selected from hydrogen, hydroxyl, alkyl, cycloalkyl, alkoxy, oxoalkyl, alkenyl, heterocyclyl, heteroaryl, cycloalkyl, aryl, aralalkyl, —C(O)CR$_6$=CH$_2$, and (CH$_2$)$_n$N$^+$(R$^a$)$_3$, where n is an integer from 1 to 16, preferably 2 to 8, and where each R$^a$ is independently H or $C_{1-4}$ alkyl;

$R_4$ and $R_5$ are independently selected from hydrogen, aryl, heterocyclyl, heteroaryl, and arylalkyl; and $R_6$ is selected from hydrogen and methyl; and $R_7$ is selected from hydrogen and —C(O)CR$_6$=CH$_2$; and preferably, at least one of $R_4$ and $R_5$ is hydrogen.

The term easier to rinse refers to the ease with which the mousse foam is rinsed away, either in terms of time taken to rinse, or how much water is required to rinse. This can be modelled by the speed at which the mousse foam collapses. The mousse foam takes less time (is quicker) to collapse in a mousse comprising the lactam and ingredient selected from phenoxyethanol, ethanol and benzoate than in the same mouse mousse without the lactam and ingredient selected from phenoxyethanol, ethanol and benzoate. The faster the mousse foam collapses, the easier it will be to rinse (taking less time, using less water etc.)

Preferably, in these uses, the lactam is a lactam selected from:

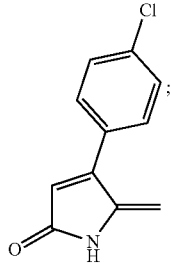

4-(4-chlorophenyl)-5-methylene-pyrrol-2-one; and

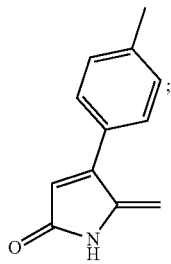

5-methylene-4-(p-tolyl)pyrrol-2-one;

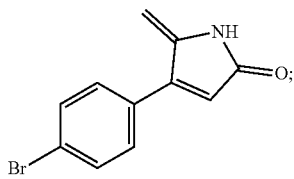

4-(4-bromophenyl)-5-methylene-pyrrol-2-one;

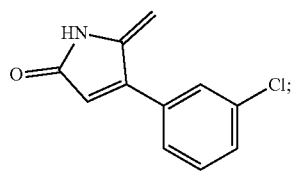

4-(3-chlorophenyl)-5-methylene-pyrrol-2-one;

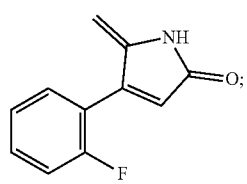

4-(2-fluorophenyl)-5-methylene-pyrrol-2-one; and

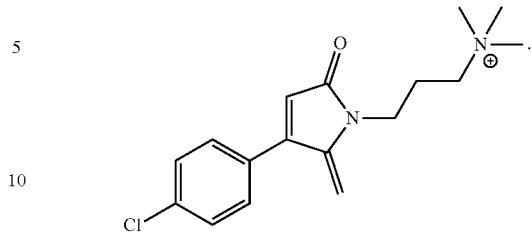

DETAILED DESCRIPTION OF THE INVENTION

The indefinite article "a" or "an" and its corresponding definite article "the" as used herein means at least one, or one or more, unless specified otherwise.

It will be appreciated that, except where expressly provided otherwise, all preferences are combinable.

Lactam

A lactam is a cyclic amide. Preferred lactams are γ-lactams which have 5 ring atoms.

Preferably the lactam is of formula (I) or (II):

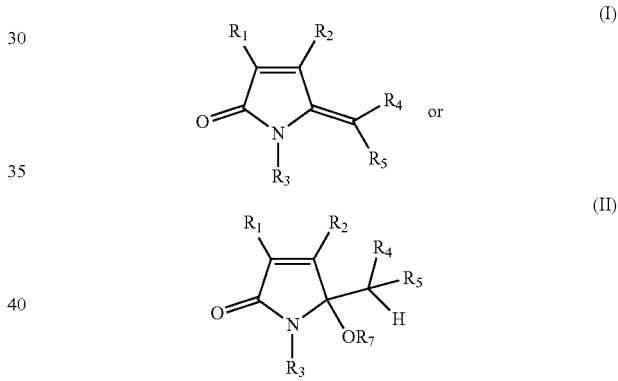

wherein:
$R_1$ and $R_2$ are each independently selected from hydrogen, halogen, alkyl, cycloalkyl, alkoxy, oxoalkyl, alkenyl, heterocyclyl, heteroaryl, aryl and aralalkyl; and $R_3$ is selected from hydrogen, hydroxyl, alkyl, cycloalkyl, alkoxy, oxoalkyl, alkenyl, heterocyclyl, heteroaryl, cycloalkyl, aryl, aralalkyl, —C(O)CR$_6$═CH$_2$, and (CH$_2$)$_n$N$^+$(R$^a$)$_3$, where n is an integer from 1 to 16, preferably 2 to 8, and where each R$^a$ is independently H or C$_{1-4}$ alkyl;

$R_4$ and $R_5$ are independently selected from hydrogen, aryl, heterocyclyl, heteroaryl, and arylalkyl; and $R_6$ is selected from hydrogen and methyl; and $R_7$ is selected from hydrogen and —C(O)CR$_6$═CH$_2$; and Preferably, at least one of $R_4$ and $R_5$ is hydrogen.

It will be appreciated that, where appropriate groups may be optionally substituted. Optional substituents may include halogens, C$_{1-4}$alkyl, C$_{1-4}$haloalkyl (for example, CF$_3$) and C$_{1-4}$alkoxy.

Alkyls may, for example, be C$_{1-12}$alkyls, such as C$_{1-6}$alkyls. Aryls may, for example, be C$_{6-10}$aryls, for example, phenyls.

Preferably, at least one of $R_1$ and $R_2$ is selected from heterocyclyl, heteroaryl, aryl and arylalkyl.

Preferably, $R_1$ is hydrogen. Preferably, $R_3$ is hydrogen, or $(CH_2)_nN^+(R^a)_3$, where n is an integer from 1 to 16, preferably 2 to 8, and where each $R^a$ is independently H or $C_{1-4}$ alkyl, more preferably $R^a$ is $CH_3$; Preferably, $R_4$ is hydrogen. Preferably, $R_5$ is hydrogen. Preferably, $R_6$ is hydrogen. Preferably, $R_7$ is hydrogen. Preferably, $R_2$ is aryl or aralalkyl. More preferably, $R_2$ is a phenyl group or a substituted phenyl group, for example, a mono-substituted phenyl group. Substitution may be ortho, meta, or para. Preferred substituents include halogen and methyl. For example, and without limitation, $R_2$ may be selected from phenyl, 4-fluorophenyl, 2-fluorophenyl, 4-chlorophenyl, 3-chlorophenyl, 4-bromophenyl and 4-methylphenyl.

More preferably in the lactam of formula (I) or (II), $R_1$, $R_4$ and $R_5$ are H; $R_3$ is H, or $(CH_2)_nN^+(CH_3)_3$, where n is an integer from 1 to 16, preferably 2 to 8; and $R_2$ is a phenyl group, or a mono-substituted phenyl group; preferably $R_2$ is selected from phenyl, 4-fluorophenyl, 2-fluorophenyl, 4-chlorophenyl, 3-chlorophenyl, 4-bromophenyl and 4-methylphenyl.

Even more preferably the lactam is of formula (I), $R_1$, $R_4$ and $R_5$ are H; $R_3$ is H, or $(CH_2)_nN^+(CH_3)_3$, where n is an integer from 1 to 16, preferably 2 to 8; and $R_2$ is a phenyl group, or a mono-substituted phenyl group; preferably $R_2$ is selected from phenyl, 4-fluorophenyl, 2-fluorophenyl, 4-chlorophenyl, 3-chlorophenyl, 4-bromophenyl and 4-methylphenyl.

Where the lactam is cationic in nature, it can be used as such, or suitably with a counterion (e.g. iodide)

Preferably the lactam is a lactam selected from:

5-methylene-4-(p-tolyl)pyrrol-2-one;

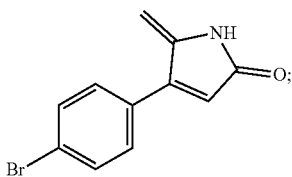

4-(4-bromophenyl)-5-methylene-pyrrol-2-one;

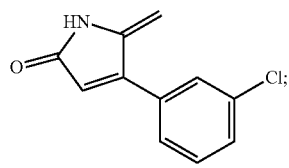

4-(3-chlorophenyl)-5-methylene-pyrrol-2-one;

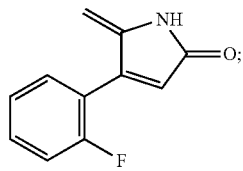

4-(2-fluorophenyl)-5-methylene-pyrrol-2-one; and

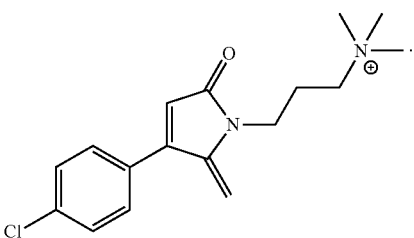 [SMILES: C=C1C(c2ccc(Cl)cc2)=CC(=O)N1CCC[N+](C)(C)C]

Where the lactam is cationic in nature, the cation can be used or with a suitable counterion (e.g. iodide).

More preferably the lactam is a lactam selected from:

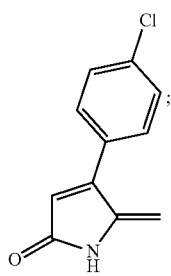

4-(4-chlorophenyl)-5-methylene-pyrrol-2-one; and

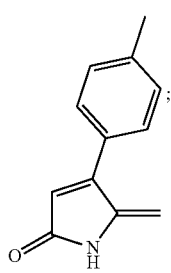

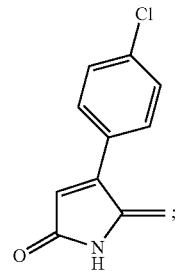

4-(4-chlorophenyl)-5-methylene-pyrrol-2-one; and

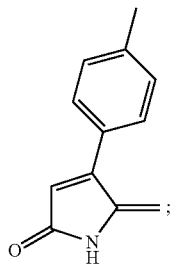

5-methylene-4-(p-tolyl)pyrrol-2-one;

Most preferably the lactam is:

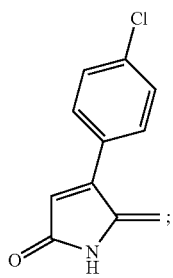

4-(4-chlorophenyl)-5-methylene-pyrrol-2-one.

Preferably the lactam is encapsulated.

Suitably, the encapsulated lactam is a polymer encapsulated lactam.

The encapsulated lactam may be encapsulated in a polymer selected from a poly urea polymer, a melamine-formaldehyde copolymer; a urea formaldehyde copolymer and mixtures thereof.

Suitably the polymer is a condensation polymer. For example, the polymer may be a condensation polymer of produced from a diamine and a disocyanate.

For example, the polymer may be or may comprise a polyurea of Formula P1:

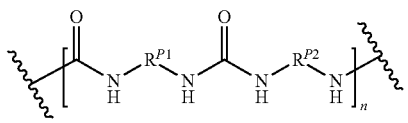

wherein $R^{P1}$ comprises a phenylene and $R^{P2}$ is an alkylene.

For example, $R^{P1}$ may be —CH$_2$-phenylene; in other words, the polymer may be derived from polymethylene polyphenyl isocyanate.

For example, $R^{P2}$ may be a straight chain alkylene of formula —(CH$_2$)$_m$—. In some cases, m is an integer from 2 to 10, for example from 2 to 8, for example from 4 to 8, for example, 6 (in other words, $R^{P2}$ may be hexylene).

In other words, the lactam may be encapsulated in a polymer formed from polymethylene polyphenyl isocyanate and hexamethylenediamine.

In some cases, the polymer and/or encapsulate structure is selected and/or configured to permit controlled or triggered release. For example, the encapsulate may dissolve at a pre-determined rate under certain conditions. For example, the encapsulate may release in response to a trigger. The trigger may be, for example, the presence or a certain concentration of acid, base, a salt, an enzyme; or a non-chemical trigger such as ultrasound or light.

Suitably, the lactam is encapsulated to form particles whose average diameter is from about 10 nanometers to about 1000 microns, preferably from about 50 nanometers to about 100 microns, more preferably from about 2 to about 40 microns, even more preferably from about 4 to 15 microns. A particularly preferred range is from about 5 to 10 microns, for example 6 to 7 microns. The capsule distribution can be narrow, broad or multimodal. Multimodal distributions may be composed of different types of capsule chemistries.

The encapsulation process suitably is done in a carrier oil, which may be a ketone. For example, the carrier oil may be a $C_{5-20}$alkyl ketone, for example a $C_{5-15}$alkyl ketone, for example a $C_{5-10}$alkyl ketone, for example a $C_{6-8}$alkyl ketone, such as a $C_7$alkyl ketone. The alkylketone may be branched or straight-chain. Preferably, it is straight chain. The oxo group of the alkyl ketone may be located at C2; in other words, the alkylketone may be an alkyl-2-one. A preferred carrier oil is 2-heptanone.

Levels of Lactam

Preferably the lactam is present at a level of from 0.0001 to 2.5 wt. %, preferably from 0.0001 to 1 wt. %. For example, the lactam may be suitably present at levels of 0.001 to 1 wt. %, or even 0.01 to 1 wt. %, or even 0.01 to 0.5 wt. %.

Alcohol

The base composition comprises from 0.1 to 5 wt. %, preferably from 0.25 to 4 wt. % of an alcohol.

More preferably the alcohol contains from 2 to 12 carbon atoms, i.e. a $C_2$-$C_{12}$ alcohol, inclusive of alkyl and/or aryl based alcohols. More preferably the alcohol is a primary alcohol.

Preferably the alcohol is selected from the group consisting of: phenoxyethanol and ethanol, inclusive of mixtures thereof.

Propellant

The mousse comprises a propellant.

Preferred propellants are selected from: one or more $C_3$-$C_5$ saturated alkanes or mixtures thereof and dimethyl ether.

The propellant can suitably be one or more $C_3$-$C_5$ saturated alkanes, including straight chain and branched hydrocarbons. Examples include propane, i-butane, n-butane, i-pentane, n-pentane. Preferably the propellant is a mixture of propane, i-butane, and n-butane. Commercially available propellants include AP40.

Preferably the base composition is present at a level of from 80 to 96 wt. %; and the propellant is present at a level of from 4 to 20 wt. %, preferably the base composition is present at a level of from 85 to 95 wt. %; and the propellant is present at a level of from 5 to 15 wt. %. More preferably the base composition is present at a level of from 88 to 95 wt. %; and the propellant is present at a level of from 5 to 12 wt. %.

Preferably the base composition comprises one or more of the following ingredients: surfactants, solvents, perfumes, preservatives, thickeners, chelating agents, emulsifiers, pH modifiers, soil removal aids and, hydrotrope.

Solvent

The mousse composition may comprise one or more solvents. Preferred solvent levels range from 60 to 95 wt. %, more preferably from 70 to 90 wt. %. A suitable and preferred solvent is water.

11

Surfactant

The mousse composition may comprise one or more surfactants.

Preferred surfactant levels range from 0.1 to 20 wt. %, more preferably from 0.25 to 18 wt. %, most preferably from 0.5 to 15 wt. %.

Any suitable surfactant may be used, including for example, anionic, nonionic, cationic and amphoteric surfactants.

Preferably the surfactant is selected from anionic and nonionic surfactants.

Suitable anionic detergent compounds which may be used are usually water-soluble alkali metal salts of organic sulphates and sulphonates having alkyl radicals containing from about 8 to about 22 carbon atoms, the term alkyl being used to include the alkyl portion of higher alkyl radicals.

Examples of suitable synthetic anionic detergent compounds are sodium and potassium alkyl sulphates, especially those obtained by sulphating higher $C_8$ to $C_{18}$ alcohols, produced for example from tallow or coconut oil, sodium and potassium alkyl $C_9$ to $C_{20}$ benzene sulphonates, particularly sodium linear secondary alkyl $C_{10}$ to $C_{15}$ benzene sulphonates; and sodium alkyl glyceryl ether sulphates, especially those ethers of the higher alcohols derived from tallow or coconut oil and synthetic alcohols derived from petroleum.

The anionic surfactant is preferably selected from: linear alkyl benzene sulphonate; alkyl sulphates; alkyl ether sulphates; soaps (including fatty acids such as lauric acid or fatty acid mixtures); alkyl (preferably methyl) ester sulphonates, and mixtures thereof.

The most preferred anionic surfactants are selected from: linear alkyl benzene sulphonate; alkyl sulphates; alkyl ether sulphates and mixtures thereof. Preferably the alkyl ether sulphate is a $C_{12}$-$C_{14}$ n-alkyl ether sulphate with an average of 1 to 3EO (ethoxylate) units.

Sodium lauryl ether sulphate is particularly preferred (SLES). Preferably the linear alkyl benzene sulphonate is a sodium $C_{11}$ to $C_{15}$ alkyl benzene sulphonates. Preferably the alkyl sulphate is a linear or branched sodium $C_{12}$ to $C_{18}$ alkyl sulphates. Sodium dodecyl sulphate is particularly preferred, (SDS, also known as primary alkyl sulphate).

It is possible for two or more anionic surfactants to be present, for example linear alkyl benzene sulphonate together with an alkyl ether sulphate.

Suitable nonionic detergent compounds which may be used include, in particular, the reaction products of compounds having an aliphatic hydrophobic group and a reactive hydrogen atom, for example, aliphatic alcohols, acids or amides, especially ethylene oxide either alone or with propylene oxide. Preferred nonionic detergent compounds are the condensation products of aliphatic $C_8$ to $C_{18}$ primary or secondary linear or branched alcohols with ethylene oxide. Alternative nonionic surfactants include alkyl polyglycoside (APG).

Preferably the surfactants used are saturated.

More preferably the surfactant comprises nonionic surfactants, more preferably alcohol ethoxylates.

Most preferably the nonionic surfactant is a $C_8$ to $C_{18}$ primary alcohol with an average ethoxylation of 7EO to 9EO units.

Amphoteric surfactants such as cocamidopropyl betaine (CAPB) can also be included. Preferably such a surfactant is included as part of a surfactant mixture with an anionic and/or nonionic surfactant.

12

Chelant

A chelating agent is preferably included in the mousse formulation. Typical inclusion levels are from 0.01 to 2.5 wt. %, preferably 0.025 to 1 wt. %.

The chelant may preferably be: citric acid; EDTA (ethylenediaminetetraacetic acid) or a phosphonic acid.

Example phosphonic acid (or phosphonate salt thereof) chelating agents are: 1-Hydroxyethylidene-1,1-diphosphonic acid (HEDP); Diethylenetriaminepenta(methylenephosphonic acid) (DTPMP); Hexamethylenediaminetetra(methylenephosphonic acid) (HDTMP); Aminotris(methylenephosphonic acid) (ATMP); Ethylenediaminetetra(methylenephosphonic acid) (EDTMP); Tetramethylenediaminetetra(methylenephosphonic acid) (TDTMP); and, Phosphonobutanetricarboxylic acid (PBTC); and salts thereof.

Thickeners

Suitable thickeners a preferably selected from hydroxyethyl cellulose, styrene/acrylates copolymers and cross-linked polyacrylic acid.

pH Modifiers

These can be used to modify the pH to the appropriate level. For cleaning purposes, it can be useful to have an alkaline pH, in which case NaOH is a useful pH modifier.

The mousse composition may additionally comprise one or more of: emulsifiers, perfumes, preservatives, and, hydrotrope.

The invention will be further described with the following non-limiting examples.

EXAMPLES

Example 1—Preparation of Examples of Preferred Lactams

Preparation of 4-(4-chlorophenyl)-5-hydroxy-5-methylfuran-2(5H)-one

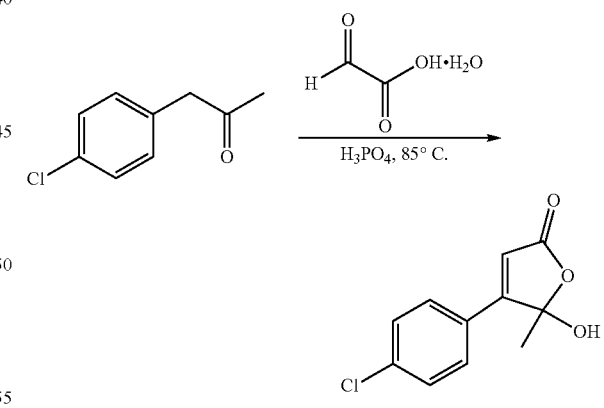

1-(4-Chlorophenyl)propan-2-one (40.00 g, 34.75 mL, 237.2 mmol), glyoxylic acid monohydrate (32.75 g, 355.8 mmol) and phosphoric acid (69.74 g, 711.7 mmol) were combined at room temperature before heating to 85° C. overnight. After cooling to room temperature, the mixture was poured into a mixture of water (500 mL) and ethyl acetate (500 mL). The layers were separated and the aqueous phase extracted with ethyl acetate (500 mL). The combined organic layers were washed with a 1:1 mixture of water and brine (2×500 mL), dried (MgSO$_4$) and concentrated under reduced pressure to yield 4-(4-chlorophenyl)-5-hydroxy-5- methylfuran-2(5H)-one (66.00 g, >100% yield) as a brown oil. The material was used in the next step without further purification.

Preparation of 4-(4-chlorophenyl)-5-hydroxy-5-methyl-1H-pyrrol-2(5H)-one

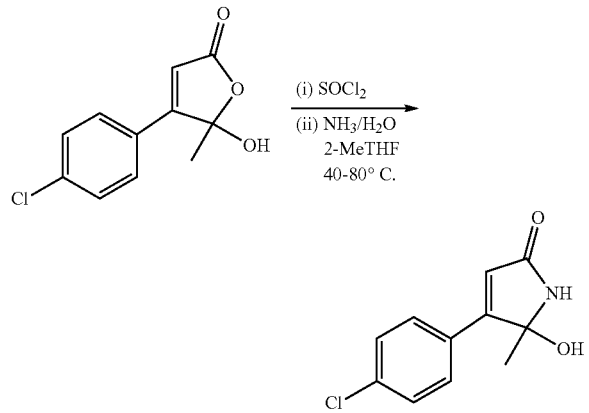

4-(4-Chlorophenyl)-5-hydroxy-5-methylfuran-2(5H)-one (66.00 g, 293.8 mmol) was dissolved in thionyl chloride (196.8 g, 120.0 mL, 1654 mmol) and heated at 40° C. for 1 hour, then 80° C. for 2 hours. The mixture was concentrated under reduced pressure and azeotroped with 2-methyltetrahydrofuran (200 mL). The residue was diluted with 2-methyltetrahydrofuran (160 mL) and this solution added to a cooled stirring mixture of 28% ammonia in water (180 mL) in 2-methyltetrahydrofuran (20 mL) at 0° C. The mixture was warmed to room temperature and stirred overnight. Water (100 mL) and ethyl acetate (200 mL) were added and the layers separated. The aqueous phase was extracted with ethyl acetate (200 mL), and the combined organic extracts dried (MgSO₄) and concentrated under reduced pressure. Purification by dry flash column chromatography (5-60% ethyl acetate in heptane) yielded 4-(4-chlorophenyl)-5-hydroxy-5-methyl-1H-pyrrol-2(5H)-one (23.18 g, 35% yield) as a cream coloured solid.

$^1$H NMR (400 MHz, d$_6$-DMSO) 8.55 (brs, 1H), 7.88-7.83 (m, 2H), 7.51-7.46 (m, 2H), 6.37 (d, 1H), 6.32 (s, 1H), 1.45 (s, 3H)

UPLC (Basic) 1.51/5.00 min, 100% purity, M+H$^+$ 224

MP 177° C.

Preparation of 4-(4-chlorophenyl)-5-methylene-1H-pyrrol-2(5H)-one

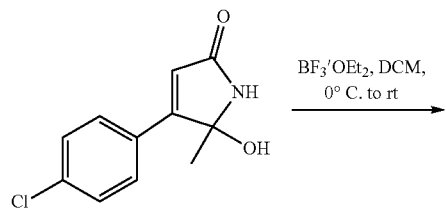

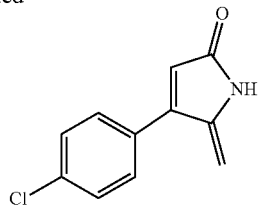

To a cooled solution of 4-(4-chlorophenyl)-5-hydroxy-5-methyl-1H-pyrrol-2(5H)-one (10.00 g, 44.51 mmol) in dry dichloromethane (100 mL) at 0° C. was added a solution of boron trifluoride diethyl etherate (8.213 g, 7.142 mL, 57.87 mmol) in dry dichloromethane (45 mL) over 15 minutes. The mixture was stirred at 0° C., before slowly warming to room temperature and stirring for 2 hours. The reaction was quenched with ice-water (100 mL) and the layers separated. The aqueous layer was extracted with dichloromethane (100 mL), and the combined organic layers washed with a 1:1 mixture of water and saturated aqueous sodium hydrogen carbonate solution (100 mL), dried (MgSO₄) and filtered. Silica was added to the filtrate and the mixture stirred for 10 minutes before filtering through a plug of silica, washing through with dichloromethane followed by a 3:1 mixture of dichloromethane:diethyl ether. Fractions containing the desired product were combined and concentrated under reduced pressure. Upon concentration a precipitate formed, which was collected by filtration, washing with diethyl ether, to yield 4-(4-chlorophenyl)-5-methylene-1H-pyrrol-2(5H)-one (5.25 g, 57% yield) as a cream coloured solid.

$^1$H NMR (400 MHz, d$_6$-DMSO) 10.10 (s, 1H), 7.54-7.47 (m, 4H), 6.36 (s, 1H), 5.04 (t, 1H), 4.85 (s, 1H)

UPLC (Basic) 1.87/5.00 min, 100% purity, M+H$^+$ 206

MP 182° C.

Preparation of 5-hydroxy-5-methyl-4-(p-tolyl)furan-2(5H)-one

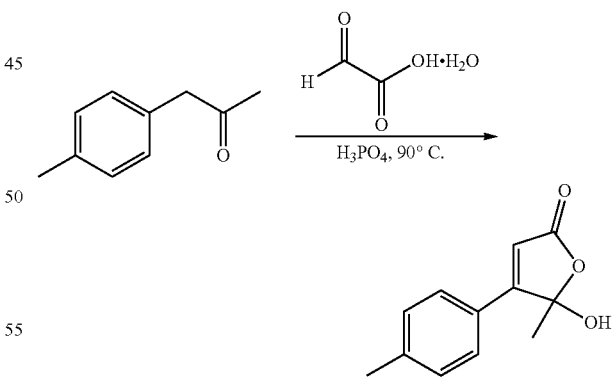

1-(p-Tolyl)propan-2-one (25.00 g, 24.00 mL, 168.7 mmol), glyoxylic acid monohydrate (23.29 g, 253.0 mmol) and phosphoric acid (49.60 g, 506.1 mmol) were combined at room temperature before heating at 90° C. overnight. After cooling to room temperature, the mixture was poured into a stirring mixture of ice-water (400 mL) and ethyl acetate (400 mL). The layers were separated and the organic phase washed with water (100 mL), dried (MgSO₄) and concentrated under reduced pressure. The mixture was azeotroped with 2-methyltetrahydrofuran (50 mL) to yield 5-hydroxy-5-methyl-4-(p-tolyl)furan-2(5H)-one (16.50 g, 48% yield) as a brown solid.

$^1$H NMR (400 MHz, d$_6$-DMSO) 7.86 (s, 1H), 7.75 (d, 2H), 7.28 (d, 2H), 6.59 (s, 1H), 2.32 (s, 3H), 1.61 (s, 3H)

Preparation of 5-hydroxy-5-methyl-4-(p-tolyl)-1H-pyrrol-2(5H)-one

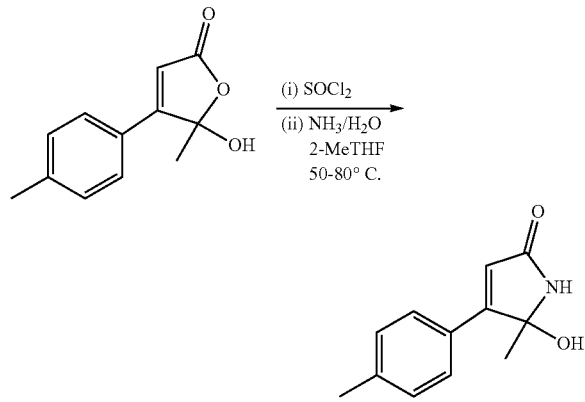

5-Hydroxy-5-methyl-4-(p-tolyl)furan-2(5H)-one (16.50 g, 80.80 mmol) was dissolved in thionyl chloride (48.06 g, 29.47 mL, 404.0 mmol) and heated at 50° C. for 1 hour, before heating at reflux for 1 hour. After cooling to room temperature, the mixture was concentrated under reduced pressure and azeotroped with 2-methyltetra-hydrofuran (2×50 mL). The residue was diluted with 2-methyltetrahydrofuran (60 mL) and this solution added to a cooled stirring mixture of 28% ammonia in water (55 mL, 808.0 mol) in 2-methyltetrahydrofuran (10 mL) at 0° C. The mixture was warmed to room temperature and stirred overnight. 2-Methyltetrahydrofuran was removed under reduced pressure, and the residue diluted with water (200 mL) and diethyl ether (100 mL) and the mixture stirred for 20 minutes at room temperature. The solids were collected by filtration and stirred in water (100 mL) and diethyl ether (50 mL) at room temperature for 10 minutes. The solids were collected by filtration and washed with water, diethyl ether and dried under vacuum at 50° C. to yield 5-hydroxy-5-methyl-4-(p-tolyl)-1H-pyrrol-2(5H)-one (10.49 g, 31% yield) as a light beige solid.

$^1$H NMR (400 MHz, d$_6$-DMSO) 8.44 (brs, 1H), 7.73 (d, 2H), 7.21 (d, 2H), 6.24 (s, 2H), 2.29 (s, 3H), 1.45 (s, 3H)

$^{13}$C NMR (400 MHz, d$_6$-DMSO) 170.4 (s, 1C), 161.1 (s, 1C), 139.8 (s, 1C), 129.7 (s, 2C), 128.9 (s, 1C), 128.2 (s, 2C), 119.1 (s, 1C), 87.8 (s, 1C), 26.7 (s, 1C), 21.5 (s, 1C)

UPLC (Basic) 1.41/5.00 min, 100% purity, M+H$^+$ 204

MP 178° C. Decomposition

Preparation of 5-methylene-4-(p-tolyl)-1H-pyrrol-2(5H)-one

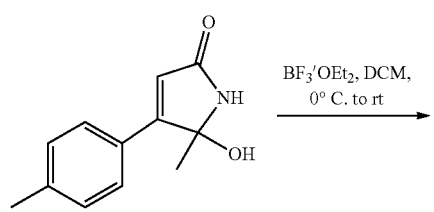

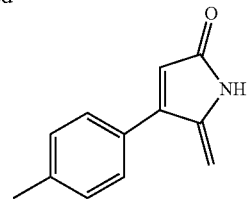

To a cooled solution of 5-hydroxy-5-methyl-4-(p-tolyl)-1H-pyrrol-2(5H)-one (8.68 g, 42.7 mmol) in dry dichloromethane (87 mL) at 0° C. was added a solution of boron trifluoride diethyl etherate (6.85 g, 5.96 mL, 55.5 mmol) in dry dichloromethane (40 mL) over 15 minutes. After 1 hour the mixture was allowed to slowly warm to room temperature. After a further 3 hours, the reaction was diluted with dichloromethane (50 mL) and ice-water (100 mL) and stirred for 10 minutes. The layers were separated and the organic layer washed with water (100 mL), a 1:1 mixture of water and saturated aqueous sodium hydrogen carbonate solution (100 mL) and brine (100 mL) and the organic layer filtered through Celite, washing with dichloromethane. Any excess water was removed by pipette before drying the filtrate (MgSO$_4$) and concentrating under reduced pressure to a brown solid. The solids were stirred in hot dichloromethane (120 mL) for 15 minutes before slowly cooling to room temperature and then 0° C. The solids were collected by filtration to yield 5-methylene-4-(p-tolyl)-1H-pyrrol-2 (5H)-one (3.87 g, 49% yield) as a yellow solid. Silica was added to the filtrate and the mixture stirred for 10 minutes before filtering through a plug of silica, washing through with dichloromethane and then a 4:1 mixture of dichloromethane:diethyl ether. The filtrate was concentrated under reduced pressure to yield 5-methylene-4-(p-tolyl)-1H-pyrrol-2(5H)-one (0.58 g, 7%) as a yellow solid. Total yield of 5-methylene-4-(p-tolyl)-1H-pyrrol-2(5H)-one (4.45 g, 56% yield).

$^1$H NMR (400 MHz, d$_6$-DMSO) 10.11 (brs, 1H), 7.35 (d, 2H), 7.25 (d, 2H), 6.25 (s, 1H), 5.01 (s, 1H), 4.85 (s, 1H), 2.31 (s, 3H)

UPLC (Basic) 1.83/5.00 min, 100% purity, M+H$^+$ 186

MP 200° C. Decomposition

Example 2—Lactam Incorporation in Mousse Formulations

Base Formulations

Required water volume was placed into the beaker and placed under the overhead stirrer at 220 rpm.

The ingredients were added in this order:

Ethanol if required.

Addition of polymers—beginning with solid polymers; these were shaken gently into the water to avoid aggregation and clumping. Each polymer was allowed to disperse for 5-10 min @ 220 rpm before addition of next polymer.

Agitation was stopped before adding liquid polymers and mixing for 5-10 minutes at 220 rpm.

Addition of surfactants to the mix at 220 rpm until fully dispersed.

Addition of silicones once the surfactant system has been incorporated for 10 minutes.

Addition of fragrance for 10 mins.

Once fully disperse the formulation was decanted through a filter into an appropriate sized container.

The lactam powder (4-(4-chlorophenyl)-5-methylene-pyrrol-2-one) was post dosed into the variant formulations at 100 mg/l final concentration and mixed for 5-10 minutes until no visible powder remained. This equated to 0.01 wt. % of lactam in the formulation.

The pH of the formulations was typically 5.5-6.5. Formulations were stored for 1-2 days before gassing.

Phenoxyethanol Mousse Formulation

| Ingredient | wt. % |
| --- | --- |
| DC 7113 | 0.91 |
| Advantage S | 0.2275 |
| Celquat L200 | 1.5925 |
| propylene glycol | 0.91 |
| tego betaine F50 | 0.364 |
| Ercasol 13LH | 0.182 |
| Fab AO | 0.3 |
| Tween 20 | 0.182 |
| dissolvine NA | 0.141 |
| water | to 100 |
| phenoxethanol | 0.7 |
| lactam | 0.01 |
| Lexguard O | 0.4 |
| EDTA | 0.05 |
| AP40 | 9 |

Benzoate Mousse Formulation

| Ingredient | wt. % |
| --- | --- |
| DC 7113 | 0.91 |
| Advantage S | 0.2275 |
| Celquat L200 | 1.5925 |
| propylene glycol | 0.91 |
| tego betaine F50 | 0.364 |
| Ercasol 13LH | 0.182 |
| Fab AO | 0.3 |
| Tween 20 | 0.182 |
| dissolvine NA | 0.141 |
| water | to 100 |
| Sodium Benzoate | 0.5 |
| lactam | 0.01 |
| EDTA | 0.05 |
| AP40 | 9 |

Ethanol Mousse Formulation

| Ingredient | wt. % |
| --- | --- |
| DC 7113 | 0.91 |
| Advantage S | 0.2275 |
| Celquat L200 | 1.5925 |
| propylene glycol | 0.91 |
| tego betaine F50 | 0.364 |
| Ercasol 13LH | 0.182 |
| Fab AO | 0.3 |
| Tween 20 | 0.182 |
| dissolvine NA | 0.141 |
| water | to 100 |
| Ethanol | 9 |
| lactam | 0.01 |
| AP40 | 9 |

Gassing (Propellant Addition)

Required amount of base and propellant depends upon the size of the can and the propellant:base ratio—for this mousse it is 91% base: 9% propellant.

For gassing, base was added to the empty can, valve attached and crimped into place before placed into the gassing chamber and the required amount of gas added through the valve. Can is then safety checked in a water bath.

Example 3—Examples of Collapsing Foam Height/Speed to Collapse

The base mousse formulations with 100 mg/l (equating to 0.01 wt. % of mousse formulation) of the lactam was dispensed and the foam height speed to collapse was determined.

The lactam used was in these experiments 4-(4-chlorophenyl)-5-methylene-pyrrol-2-one:—

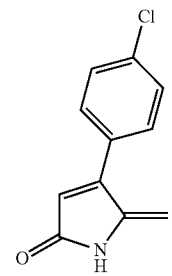

Results

| Formulation | Foam Height t = 0 min | Foam Height t = 10 min | Foam Height t = 15 min | Total time to fully collapse | % decrease in time to total foam collapse |
| --- | --- | --- | --- | --- | --- |
| A - Benzoate mousse control | 15.5 cm | 7 cm | 2.5 cm | 23 mins 30 s | |
| B - Benzoate mousse control + lactam (100 ppm) | 13.5 cm | 8 cm | 3 cm | 20 mins 43 s | 12% quicker |
| C - Ethanol mousse control | 16.0 cm | 9 cm | 3 cm | 17 mins 37 s | |
| 1 - Ethanol mousse control + lactam (100 ppm) | 15.5 cm | foam collapsed | foam collapsed | 7 mins 18 s | 59% quicker |
| D - Phenoxyethanol mousse control | 17.5 cm | foam collapsed | foam collapsed | 8 mins 35 s | |
| 2 - Phenoxyethanol mousse control + lactam (100 ppm) | 15.0 cm | foam collapsed | foam collapsed | 3 mins 5 s | 64% quicker |

The mousse height was measured after dispensing, again after 10 minutes and after 15 minutes. The time taken for the foam to fully collapse was also measured (whether longer of shorter than the 5 or 10 minute measured intervals). The % decrease in time to total foam collapse was calculated. This was done by converting the time to fully collapse into seconds, then taking the + lactam time away from the control time and then dividing by the total time of the control. For example, for ethanol, the calculation is 17 mins 37 s (=1057 s) −7 mins 18 s (=438 s)=619 s; 619/1057=59% decrease in time taken to total foam collapse.

It can be seen that the lactam had the greatest effect on foam reduction for the alcohol containing formulations (ethanol and phenoxyethanol).

This example shows that the combination of lactam with different alcohols gave rise to quick collapsing foam in comparison to the combination of lactam with benzoate. This quicker collapsing foam results in a mousse foam that is easier and quicker to rinse. The combination of lactam with alcohol gave rise to quick collapsing foam in comparison with alcohol on its own.

Example 4—Anti-Microbial Effect of Lactam Mousses

The antimicrobial impact of lactam in mousse formulations was tested on the surface of agar plates seeded with a Quorum Sensing reporter strain (*Chromobacterium violaceum*) employing the zone of inhibition assay.

Bacterial Preparation

Bacteria were subbed from the master plate onto a fresh TSA plate, using a sterile loop.

The plate was then incubated for 24 hrs at 28° C. Fresh Nutrient agar media was prepared in clean 500 ml bottles then sterilised and left to cool within 48° C. water bath until required. Inoculum was prepared using the overnight sub culture prepared on TSA. A sweep of cells was taken from TSA plate using a sterile loop-full and placed into sterile Nutrient broth. The density of the cells was adjusted using a Densimat, to a measurement of around 1.8 McFarland's (~1.5×10e8 cells/ml).

Each Nutrient agar broth (500 ml) was removed from the water bath and cooled to around 40° C. then inoculated with 7 mls of the above cell suspension (1.8×10e8 cells/ml).

Using inoculated nutrient agar a series of pour plates was generated and left to set before treatment with three separate foam formulations Dispensing of test mousse performed as follows:—

Each test container was shaken for 10 seconds and mousse was then dispensed onto four replicate Nutrient agar plates, previously prepared and inoculated with *Chromobacterium violaceum*. The foam on the plates was allowed to collapse then all lids were replaced, and agar plates incubated for 48 hrs at 28° C.

Plates were removed from the incubator and images were taken and evaluated using bespoke densitometric software.

Benzoate+lactam treated plates demonstrate little effect on microbial communication on the surface (lack of white colour) and/or reduction of growth. Alcohol+lactam treated plates showed inhibition. When the alcohol was phenoexyethanol, the mousses show considerable inhibition and when the alcohol was ethanol, the strongest inhibition was seen.

The combination of lactam with alcohol gave inhibition to microorganism growth that was much improved compared to the alcohol on its own.

This shows that the combination of lactam with different alcohols gave rise to quick collapsing foam. This combination also gave the best inhibition of microorganism growth.

The control (base) formulations were as identified in example 2 and used in example 3.

The lactam used was in these experiments 4-(4-chlorophenyl)-5-methylene-pyrrol-2-one:—

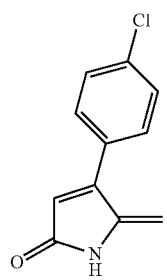

Results 4 plates for each formulation were tested.

The area of the agar plate that still had microbe present is the area in purple. Where inhibition has taken place, the area is in white to show lack of microbe. The reason why the white area is only a small proportion of the purple area for the working embodiments of the invention is because the agar plate was a large area in comparison to the small area of application of the mousse composition onto the agar plate. So after the table of results, for each mousse formulation a description of the inhibition of the microbe treated agar by the area of actual mousse application is given.

| A - Benzoate mousse control | Area of Purple | Area of White | % inhibition (area of white/area of purple) |
|---|---|---|---|
| Plate 1 | 2,155,230 | 0 | 0% |
| Plate 2 | 2,237,360 | 0 | 0% |
| Plate 3 | 2,313,790 | 1,101 | 0.05% |
| Plate 4 | 2,405,790 | 0 | 0% |

The benzoate mousse control (A) provided almost 0% inhibition (area of white/area of foam application)

| B - Benzoate mousse control + lactam (100 ppm) | Area of Purple | Area of White | % inhibition (area of white/area of purple) |
|---|---|---|---|
| Plate 1 | 2,581,630 | 0 | 0% |
| Plate 2 | 2,537,080 | 42,355 | 2% |
| Plate 3 | 2,412,640 | 0 | 0% |
| Plate 4 | 2,434,320 | 2,956 | 0.1% |

The benzoate mousse control+lactam (B) provided <15% inhibition (area of white/area of foam application)

| C - Ethanol mousse control | Area of Purple | Area of White | % inhibition (area of white/area of purple) |
|---|---|---|---|
| Plate 1 | 2,440,510 | 0 | 0 |
| Plate 2 | 2,281,280 | 0 | 0 |
| Plate 3 | 2,566,680 | 0 | 0 |
| Plate 4 | 2,519,800 | 0 | 0 |

The ethanol mousse control (C) provided almost 0% inhibition (area of white/area of foam application)

| 1 - Ethanol mousse control + lactam (100 ppm) | Area of Purple | Area of White | % inhibition (area of white/area of purple) |
|---|---|---|---|
| Plate 1 | 2,051,380 | 501,900 | 24.5% |
| Plate 2 | 2,166,660 | 361,081 | 16.7% |
| Plate 3 | 1,935,830 | 570,370 | 29.5% |
| Plate 4 | 1,944,950 | 636,663 | 32.7% |

The ethanol mousse control+lactam (1) provided almost 100% inhibition (area of white/area of foam application)

| D - Phenoxyethanol mousse control | Area of Purple | Area of White | % inhibition (area of white/area of purple) |
|---|---|---|---|
| Plate 1 | 2,220,900 | 0 | 0 |
| Plate 2 | 2,271,310 | 0 | 0 |

-continued

| D - Phenoxyethanol mousse control | Area of Purple | Area of White | % inhibition (area of white/area of purple) |
|---|---|---|---|
| Plate 3 | 2,726,870 | 0 | 0 |
| Plate 4 | 2,714,000 | 0 | 0 |

The phenoxyethanol mousse control (D) provided 0% inhibition (area of white/area of foam application)

| 2 - Phenoxyethanol mousse control + lactam (100 ppm) | Area of Purple | Area of White | % inhibition (area of white/area of purple) |
|---|---|---|---|
| Plate 1 | 2,122,500 | 305,289 | 14.4% |
| Plate 2 | 1,839,850 | 553,899 | 30.1% |
| Plate 3 | 1,689,280 | 488,827 | 28.9% |
| Plate 4 | 1,804,970 | 472,954 | 26.2% |

The phenoxyethanol mousse control+lactam (2) provided ~80% inhibition (area of white/area of foam application)

The inhibition can be seen by the application of the lactam. The inhibitory effects of the lactam in combination with the two different alcohols was most pronounced. The inhibitory effects of the lactam where the foam was actually applied to the agar was most especially pronounced for the lactam in combination with the two different alcohols (ethanol and phenoxyethanol) where approx. 80-100% inhibition was seen.

The invention claimed is:

1. A mousse composition comprising:
a) a base composition comprising:
   i. from 0.0001 to 5 wt. % of a lactam;
   ii. from 0.1 to 5 wt. % of an alcohol; and,
b) a propellant,
wherein the lactam is of formula (I) or (II):

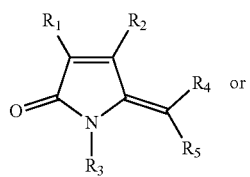

(I)

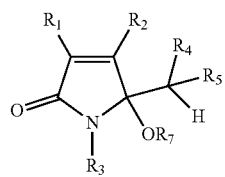

(II)

wherein:
$R_1$ and $R_2$ are each independently selected from hydrogen, halogen, alkyl, cycloalkyl, alkoxy, oxoalkyl, alkenyl, heterocyclyl, heteroaryl, aryl and aralalkyl; and
$R_3$ is selected from hydrogen, hydroxyl, alkyl, cycloalkyl, alkoxy, oxoalkyl, alkenyl, heterocyclyl, heteroaryl, cycloalkyl, aryl, aralalkyl, —C(O)CR$_6$=CH$_2$, and (CH$_2$)$_n$N$^+$(R$^a$)$_3$, where n is an integer from 1 to 16, and where each R$^a$ is independently H or C$_{1-4}$ alkyl;
$R_4$ and $R_5$ are independently selected from hydrogen, aryl, heterocyclyl, heteroaryl, and arylalkyl; and
$R_6$ is selected from hydrogen and methyl; and
$R_7$ is selected from hydrogen and —C(O)CR$_6$=CH$_2$.

2. A mousse composition according to claim 1, wherein the lactam is present at a level of from 0.0001 to 2.5 wt. %.

3. A mousse composition according to claim 1, wherein the alcohol is selected from the group consisting of: phenoxyethanol and ethanol, inclusive of mixtures thereof.

4. A mousse composition according to claim 1, wherein in the lactam of formula (I) or (II), $R_1$, $R_4$ and $R_5$ are H; $R_3$ is H, or (CH$_2$)$_n$N$^+$(CH$_3$)$_3$, where n is an integer from 1 to 16; and $R_2$ is a phenyl group, or a mono-substituted phenyl group.

5. A mousse composition according to claim 1, wherein the lactam is a lactam selected from:

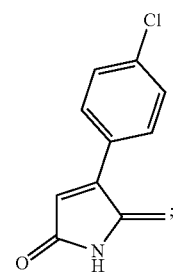

4-(4-chlorophenyl)-5-methylene-pyrrol-2-one; and

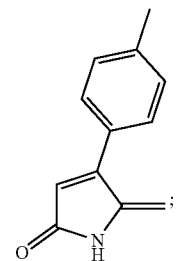

5-methylene-4-(p-tolyl)pyrrol-2-one;

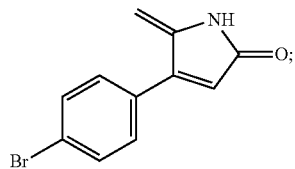

4-(4-bromophenyl)-5-methylene-pyrrol-2-one;

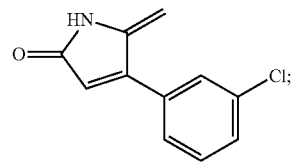

4-(3-chlorophenyl)-5-methylene-pyrrol-2-one;

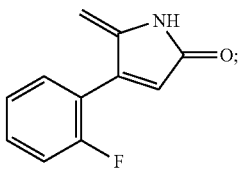

4-(2-fluorophenyl)-5-methylene-pyrrol-2-one; and

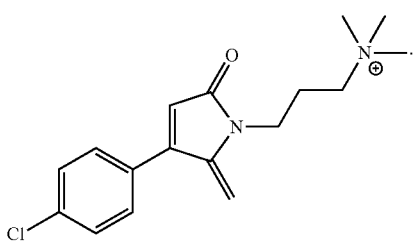 [SMILES: C=C1C(c2ccc(Cl)cc2)=CC(=O)N1CCC[N+](C)(C)C]

6. A mousse composition according to claim 1, wherein the lactam is a lactam selected from:

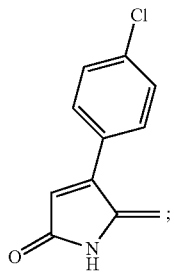

4-(4-chlorophenyl)-5-methylene-pyrrol-2-one; and

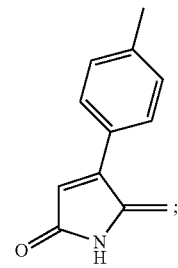

5-methylene-4-(p-tolyl)pyrrol-2-one.

7. A mousse composition according to claim 1, wherein the lactam is in encapsulated form.

8. A mousse composition according to claim 1, wherein the base composition is present at a level of from 80 to 96 wt. %; and the propellant is present at a level of from 4 to 20 wt. %.

9. A mousse composition according to claim 1, wherein the propellant is selected from: one or more $C_3$-$C_5$ saturated alkanes or mixtures thereof and dimethyl ether.

10. A mousse composition according to claim 1, wherein the base composition comprises one or more of the following ingredients: surfactants, solvents, perfumes, preservatives, thickeners, chelating agents, emulsifiers, pH modifiers, soil removal aids and, hydrotrope.

11. A mousse composition according to claim 1, where n is an integer from 2 to 8.

12. A mousse composition according to claim 1, where at least one of $R_4$ and $R_5$ is hydrogen.

13. A mousse composition according to claim 2, where the lactam is present at a level from 0.0001 to 1 wt. %.

14. A mousse composition according to claim 2, where the lactam is present at a level from 0.001 to 1 wt. %.

15. A mousse composition according to claim 4, where n is an integer from 2 to 8.

16. A mousse composition according to claim 4, where $R_2$ is selected from phenyl, 4-fluorophenyl, 2-fluorophenyl, 4-chlorophenyl, 3-chlorophenyl, 4-bromophenyl and 4-methylphenyl.

17. A mousse composition according to claim 8, wherein the base composition is present at a level of from 85 to 95 wt. % and the propellant is present at a level of from 5 to 15 wt. %.

* * * * *